United States Patent [19]

Fisher et al.

[11] Patent Number: 5,124,328
[45] Date of Patent: Jun. 23, 1992

[54] MORPHOLINE DERIVATIVES COMPOSITIONS AND USE

[75] Inventors: Michael H. Fisher, Ringoes; Matthew J. Wyvratt, Mountainside, both of N.J.

[73] Assignee: Merck & Co., Inc., Rahway, N.J.

[21] Appl. No.: 767,285

[22] Filed: Sep. 26, 1991

Related U.S. Application Data

[62] Division of Ser. No. 597,976, Oct. 11, 1990, Pat. No. 5,077,290.

[51] Int. Cl.$^5$ .................. A61K 31/535; C07D 413/04
[52] U.S. Cl. ................................. 514/235.8; 514/909; 544/122
[58] Field of Search ...................... 544/122; 514/235.8, 514/909

[56] References Cited

U.S. PATENT DOCUMENTS 5,075,305 12/1991 Hobbs et al. .................... 544/122

Primary Examiner—Robert W. Ramsuer
Attorney, Agent, or Firm—David L. Rose; Joseph F. DiPrima

[57] ABSTRACT

N-substituted-2-heterocyclic morpholine derivatives and compositions made therefrom are highly active compounds having utility as growth promotion agents for animals, bronchodilators, antidepressants and anti-obesity agents.

15 Claims, No Drawings

MORPHOLINE DERIVATIVES COMPOSITIONS AND USE

This is a division of application Ser. no. 597,976, filed Oct. 11, 1990, now U./s. Pat. No. 5,077,290.

BACKGROUND OF THE INVENTION

In U.S. Pat. No. 4,358,455 to Atkinson et al. there are disclosed certain aralkyl amino ethanol heterocyclic compounds wherein the amino substituent is a phenyl alkyl group optionally substituted with various groups.

In E.P.O. 0,244,728 to Bayer there are disclosed amino alkyl pyridines wherein the amino substituents may be alkyl, cycloalkyl, aralkyl or heterocycle.

In AUS 88-314743 to Beecham morpholine derivatives of certain β-adrenergic agonists are disclosed with phenyl substituents.

SUMMARY OF THE INVENTION

The instant invention concerns certain N-Substituted-2-heterocyclic morpholine compounds wherein the morpholine ring is N-substituted with various lower alkyl, aralkyl and heteracyclic loweralkyl groups which are potent growth promotion agents. More particularly this invention relates to compounds having the structural formula:

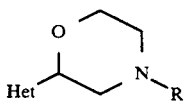

wherein Het, and R are hereinafter defined. This invention also relates to compositions having such compounds as the active ingredient for use as growth promotion agents in animals, bronchodilators, antidepressants and antiobesity agents. This invention also relates to processes for the preparation of such N-substituted-2-heterocyclic morpholine compounds.

DETAILED DESCRIPTION OF THE INVENTION

The novel compounds of the present invention are represented by the structural formula:

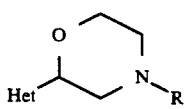

wherein
Het is

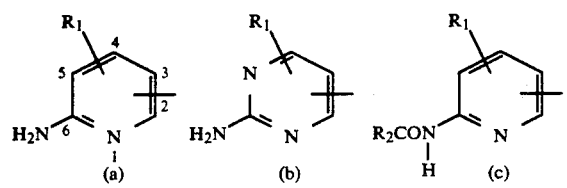

-continued

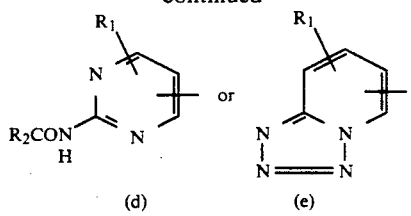

R is loweralkyl, cyclololoweralkyl aralkyl, substituted aralkyl, heterocyclicloweralkyl or substituted heterocyclicloweralkyl;

$R_1$ is hydrogen, halogen or cyano; and $R_2$ is lower alkyl, phenyl, substituted phenyl, phenyl-lower alkyl.

In the instant invention the term "lower alkyl" is intended to include those alkyl groups of either a straight or branched configuration from 1 to 8 carbons exemplified by methyl, ethyl, propyl, isopropyl, butyl, sec-butyl, tert-Butyl, emyl, hexyl and the like.

The term "cycloloweralkyl" is intended to include those cyclic alkyl groups of from 3 to 7 carbon atoms which are optionally substituted with loweralkyl.

The term "aralkyl" is intended to include loweralkyl groups substituted by aromatic hydrocarbon groups exemplified by phenyl, and naphthyl.

The substituents on the aralkyl and heterocyclicloweralkyl groups may be either on the lower alkyl portion, the aromatic hydrocarbon or the heterocyclic portions of the substituent and are exemplified by halogen, hydroxy lower alkyl, lower alkoxy, trifluoromethyl, cyano or $COOR_2$ where $R_2$ is as defined above. From 1 to 3 substituents may be present or the aralkyl group.

The term "halogen" is intended to include the halogen atoms fluorine, chlorine, bromine and iodine.

The term "heterocyclic loweralkyl" includes a lower alkyl group substituted with a heterocyclic, group exemplified by imidazolyl, and indolyl.

The term "lower alkoxy" is intended to include those alkoxy groups of from 1 to 6 carbon atoms of either a straight or branched configuration and is exemplified by methoxy, ethoxy, isopropoxy, sec butoxy, and the like.

The "substituted phenyl" substituents are from 1 to 3 of loweralkyl, hydroxy, lower alkoxy or phenyl lower alkyl.

Preferred compound of this invention are realized in the above structure when:
Het is selected from structure (a), (b), (c) or (d) or
Further preferred compounds are realized in the above structure wherein:
Het is structure (a) or (b)
Additional preferred compounds are realized wherein R is lower alkyl of from 3 to 6 carbon atoms preferably with an α-branched methyl or ethyl or an α-branched gem-dimethyl or diethyl substitution pattern; an aralkyl with an alkyl portion of from 3 to 6 carbon atoms with an α-branched methyl or ethyl or an α-branched gem dimethyl or diethyl substitution pattern and an aryl portion of phenyl, methoxyphenyl or hydroxyphenyl; and a heterocyclic loweralkyl with an alkyl portion of from 3 to 6 carbon atoms preferably α-branched methyl or ethyl or an α-branched gem dimethyl or diethyl substitution pattern and a heterocyclic portion of indolyl optionally substituted with methoxy or hydroxy;

$R_1$ is hydrogen or halogen; and $R_2$ is lower alkyl or phenyl.

The most preferred compounds of the instant invention are realized in the close formula wherein Het is structure (a) or (d);

R is tert-butyl, or 1,1-dimethylpropyl, optionally substituted with phenyl or indolyl which may then be substituted with hydroxy or methoxy; and $R_1$ is hydrogen or chloro.

Specific examples of preferred compounds are realized in the following compounds in Tables I, II, and III.

TABLE I

[Structure: 2-amino-pyridine with morpholine-containing substituent, labeled R]

R
—C(CH$_3$)$_3$
—C(CH$_3$)$_2$CH$_3$CH$_3$
—CH(CH$_3$)$_2$
—[1-methylcyclobutyl]
—CH(CH$_3$)CH$_2$—[phenyl]
—CH(CH$_3$)CH$_2$—[4-hydroxyphenyl]
—C(CH$_3$)$_2$CH$_2$—[phenyl]
—C(CH$_3$)$_2$CH$_2$CH$_2$—[4-methoxyphenyl]
—C(CH$_3$)$_2$CH$_2$CH$_2$—[3-methoxyphenyl]
—C(CH$_3$)$_2$CH$_2$CH$_2$—[2-methoxyphenyl]
—C(CH$_3$)$_2$CH$_2$—[phenyl]

TABLE I-continued

[Structure: 2-amino-pyridine with morpholine-containing substituent, labeled R]

—CH(CH$_3$)CH$_2$—[4-methoxyphenyl]
—CH(CH$_3$)CH$_2$—[indolyl]
—CH(CH$_3$)CH$_2$—[5-methoxyindolyl]
—C(CH$_3$)$_2$CH$_2$—[indolyl]
—C(CH$_3$)$_2$CH$_2$—[5-methoxyindolyl]
—C(CH$_3$)$_2$CH$_2$—[5-hydroxyindolyl]

TABLE II

[Structure: 2-aminopyrimidine with morpholine-containing substituent, labeled R]

R
—C(CH$_3$)$_3$
—C(CH$_3$)$_2$CH$_3$CH$_3$
—CH(CH$_3$)$_2$

TABLE II-continued

[Structure: 2-aminopyrimidine with exocyclic =CH- connecting to C bearing morpholine ring with N-R substituent]

| R |
|---|
| 1-methylcyclobutyl |
| —CH(CH₃)CH₂CH₂—C₆H₅ |
| —CH(CH₃)CH₂CH₂—C₆H₄—OH |
| —C(CH₃)₂CH₂CH₂—C₆H₅ |
| —C(CH₃)₂CH₂CH₂—C₆H₄—OCH₃ |
| —C(CH₃)₂CH₂CH₂—C₆H₄(m-OCH₃) |
| —C(CH₃)₂CH₂CH₂—C₆H₄(o-OCH₃) |
| —C(CH₃)₂CH₂—C₆H₅ |
| —CH(CH₃)CH₂—C₆H₄—OCH₃ |
| —CH(CH₃)CH₂—(3-indolyl) |

TABLE II-continued

[Structure: 2-amino-5-substituted pyrimidine bearing morpholine ring with N-R substituent]

| R |
|---|
| —CH(CH₃)CH₂—(5-methoxy-3-indolyl) |
| —C(CH₃)₂CH₂—(3-indolyl) |
| —C(CH₃)₂CH₂—(5-methoxy-3-indolyl) |
| —C(CH₃)₂CH₂—(5-hydroxy-3-indolyl) |

TABLE III

[Structure: 2-amino-3-chloro-5-substituted pyridine bearing morpholine ring with N-R substituent]

| R |
|---|
| —C(CH₃)₃ |
| —C(CH₃)₂CH₂CH₃ |
| —CH(CH₃)₂ |
| 1-methylcyclobutyl |
| —CH(CH₃)CH₂—C₆H₅ |
| —CH(CH₃)CH₂CH₂—C₆H₄—OH |

The optical isomeric forms, that is mixtures of enantiomers or diastereomers, e.g. racemates as well as individual enantiomers or diastereomers of the instant compounds are included within the scope of this invention. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared if desired using conventional resolution procedures, e.g., treatment with an appropriate optically active acid, separating the diastereomers and then recovering the desired isomer such as by chromatographic separation techniques. In addition, the individual optical isomers may be prepared by asymmetric synthesis.

While the carbon atom bearing the het group of the morpholine moiety is always an asymmetric center, a second asymmetric center may be found in the R group depending upon the nature of the R group.

The compounds of this invention when Het is structure (a) and (c) are prepared by the following reaction scheme:

Reaction Scheme 1

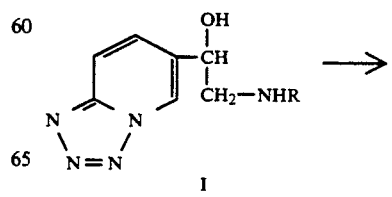

-continued
Reaction Scheme 1

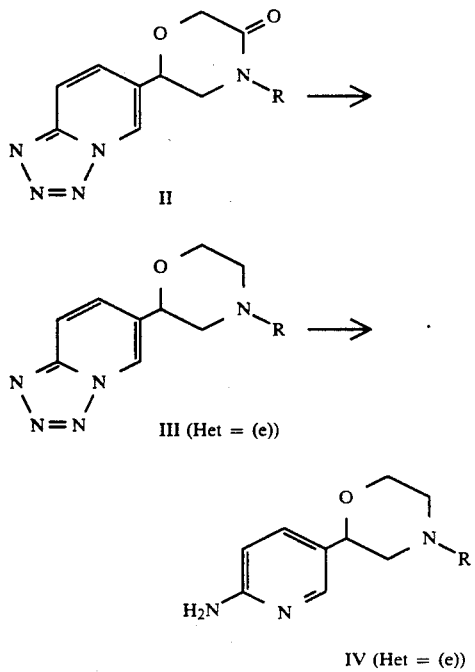

In the foregoing Reaction Scheme 1 the starting material a tetrazolyl[1,5-a]pyridyl ethanolamine (I) is described in European Patent Publication 88 202604.0. Compound I is acetylated in a ring closure reaction to prepare the 5-oxo-morpholine compound (II). The reaction is carried out in a inert solvent such as a chlorinated hydrocarbon or a hydrocarbon with chloroacetyl chloride as the preferred acetylating/ring closure reagent. It is further preferred to add at least two molecular equivalent of a non-reactive base such as a tertiary amine to react with the hydrogen chloride liberated during the course of the reaction. The reaction is carried out at from 0°6 to the reflux temperature of the reaction mixture. A preferred method is to start the reaction at the lower end of the temperature range to ensure that the reaction does not become excessively vigorous, and progress to the higher end of the temperature range to ensure that the reaction goes to completion. The reaction is generally complete in from 1 to 48 hours.

The 5-oxo-morpholine- (II) is reduced to the tetrazolyl [1,5-a] pyridyl substituted morpholine (III) using reducing agent, preferably borane-methylsulfide complex in an inert solvent such as ether, tetrahydrofuran, and the like. The reaction is carried out at from room temperature to the reflux temperature of the reaction mixture. The product is isolated using techniques known to those skilled in the art. Compound III is structure (f) where $R_1$ is hydrogen. The same procedure is used to prepare the compounds where Het is (a) and $R_1$ is to hydrogen.

The tetrazole ring of compound (III) may be removed to prepare the 2-amino pyridine, compound (IV), in an alcohol solvent such as methanol with tin (II) chloride. The addition of one equivalent of hydrogen chloride will accelerate the reaction. The reaction is heated at from 50° C. to reflux, preferably for from 1 to 24 hours, affording structure (a) where $R_1$ is hydrogen.

The compound of structures (b), (c) and (d) are prepared according to the following reaction schemes:

Scheme 2

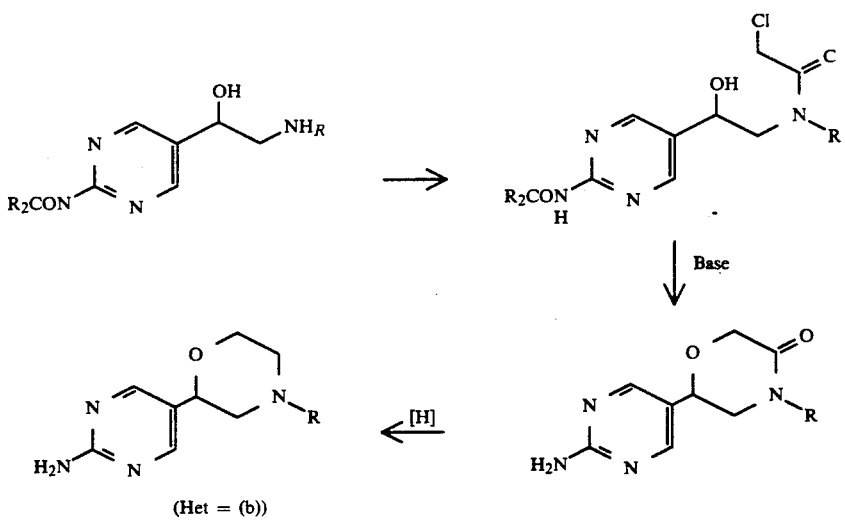

Scheme 3

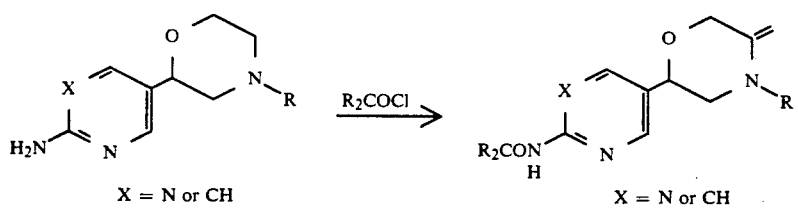

X = N or CH

X = N or CH
(Het = (c) or (d))

The same reaction conditions described above are used for the analogous step in Reaction Scheme 2. The acylation step to prepare compounds where Het is (c) or (d) is carried out with an acylating agent such as an acyl halide. The reaction is carried out under conditions known to those skilled in the art, usually in an inert solvent at from 0° C. to 100° C. and optionally in the presence of a non reactive base such as a tertary amine to react with the hydrogen halide liberated during the course of the reaction.

The compounds of this invention are capable of forming salts with various inorganic and organic acids and such salts are also within the scope of this invention. Typical acids are hydrochloric, citric, hydrobromic, sulfuric, phosphoric, methanesulfonic, toluenesulfonic, maleic, fumaric, camphorsulfonic and the like. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The compounds of this invention are useful as animal growth promotants, bronchodilators, anti-depressants and antiobesity agents.

The compounds of this invention can be used to increase the growth and feed efficiency of ruminant and non-ruminant animals such as sheep, cattle, goats, horses, swine, chickens and the like. The active compounds can be fed to the animal by incorporating them into the animal's feed or drinking water or they can be administered in a unit dosage form either orally as a drench, tablet, bolus or sustained release bolus or parenterally by injection or from a subcutaneous implant. The administration of the active compounds will produce a surprising increase in body weight, a decrease in body fat and an increase in body protein for the same food intake.

The active compounds can be administered to the animals at daily rates of from 0.001 to 10 mg/kg of body weight which may vary depending upon the particular animal being treated as well as the age and general physical condition of the animal. Preferably, daily dosages of from 0.01 to 1.0 mg/kg are utilized. When administered as part of the animal's feed or drinking water the active compound is present at rates of from 0.01 to 100 ppm which is determined to provide the appropriate daily amounts of the growth promotant compound.

At the same dosages listed above for growth promotion effects, substantial increases in feed efficiency are also observed.

Compounds of this invention also have bronchodilator activity. The compounds are thus useful to treat conditions in mammals especially human beings which benefit from bronchodilation such as asthma, etc. For use as a bronchodilator, the compound is administered orally or parenterally in conventional dosage form such as tablet, capsule, solution, dispersion, emulsion and the like. The compound may also be administered as a spray or an aerosol using an appropriate delivery device and formulation. The aerosol route is generally employed. Sufficient compound is administered to produce the desired level of bronchodilation. Daily dosages for oral or parenteral administration may range from about 1 mg to about 300 mg, and preferably from about 2 to about 150 mg. Spray or aerosol delivery will be in metered doses ranging from about 50 to about 1000 mcg, administered as needed.

The instant compounds are also useful for the treatment of clinical depression often characterized by being readily irritable or anxious with crying spells, and a lack of self confidence. The patient may have difficulty concentrating and lose interest in all usual activities including work, social activities and family. Often anorexia, chronic fatigue and either insomnia or hypersomnia may be present. Treatment is often difficult and extends over a prolonged period of time. Chemical antidepressants, such as the compounds of this invention, have been found to be helpful in the management of such depressive conditions.

The compounds of this invention promote lipolysis, the hydrolysis of fat tissue, and thus may be effective in causing weight reductions in obese patients. The compounds, as antiobesity agents, thus assist in maintaining the patient's optimum weight and further avoid the numerous physical complications associated with obesity.

For use as antidepressants and as antiobesity agents, the compounds of the present invention can be administered orally, by inhalation, by suppository or parenterally, i.e.,intravenously, intraperitoneally, etc. and in any suitable dosage form. The compounds may be offered in a form (1) for oral administration, e.g., as tablets in combination with other compounding ingredients (diluents or carriers) customarily used such as talc, vegetable oils, polyols, benzyl alcohols, starches, gelatin and the like—or dissolved, dispersed or emulsified in a suitable liquid carrier—or in capsules or encapsulated in suitable encapsulating material, or (20 for parenteral administration, dissolved, dispersed, or emulsified in a suitable liquid carrier or diluent or (3) as an aerosol or (4) as a suppository). The ratio of active ingredient (present compound) to compounding ingredients will vary as the dosage form requires. Conventional procedures are used to prepare the pharmaceutical formulations. The effective daily dosage level for the present compounds may be varied from about 10 mg to about 3000 mg. Daily doses ranging from about 100 to about 2500 mg are preferred, with about 200 to about 1000 mg being a more preferred range. Oral administration is preferred. Either single or multiple daily doses may be administered depending on unit dosage.

EXAMPLE 1

2-(Tetrazolo[1,5-a]pyrid-6-yl)-4-(1,1-dimethylethyl)-5-oxo-morpholine

To a cold (0° C.) solution of 60-[[(1,1-dimethylethyl)amino)methyl]tetrazolo[1,5-a]pyridine-6-methanol (5.6 g, 23.8 mmol) and triethylamine in 100 ml of dry (3A sieves) methylene chloride, a solution of chloroacetyl chloride (2.5 g, 26.2 mmol) in 5 ml of methylene chloride was added dropwise under nitrogen. The reaction mixture was stirred at 0° C. for 1 hour and then overnight at ambient temperature. The reaction mixture was then heated at reflux for 6 hours. The reaction mixture was concentrated under reduced pressure. The residue was dissolved in ethyl acetate and washed with water. The organic phase was dried with anhydrous magnesium sulfate and concentrated to give 7 g of crude N-chloroacetyl derivative. To an ethanolic solution (80 ml) of this crude product, a solution of sodium ethoxide in ethanol (0.53 g of sodium in 80 ml of absolute ethanol) was added slowly. The resulting solution was heated at reflux under nitrogen for 7 hours. The reaction mixture was concentrated under reduced pressure and the residue partitioned between ethyl acetate and water. The aqueous phase was further extracted with ethyl acetate and the combined organic layers were washed with saturated sodium chloride solution, dried over anhydrous magnesium sulfate and concentrated to give 4.4 g of crude cyclized product. The material was chromatographed on silica gel and eluted with 95:5 methylene chloride:ethanol to give 2.16 g of product. mass spectrum (FAB) 276 (M+1).

EXAMPLE 2

2-(Tetrazolo[1,5-a]pyrid-6-yl)-4-(1,1-dimethylethyl)-morpholine

To a solution of 2-(tetrazolo[1,5-a]pyrid-6-yl)-4-(1,1-dimethylethyl)-5-oxo-morpholine (2.09 g) in 100 ml of dry tetrahydrofuran (THF), a 2.0M solution of $BH_3.Me_2S$ in tetrahydrofuran (10 ml) was added dropwise under nitrogen. The reaction mixture was then heated at reflux for 5 hours. The mixture was cooled and treated with 25 ml of methanol. The mixture was then heated at reflux for 3 hours. The solution was concentrated under reduced pressure and the residue (2.45 g) purified by column chromatography (95:5 methylene chloride:ethanol) on silica gel to give 1.99 g of product. Mass spectrum (FAB) 262 (M+1).

EXAMPLE 3

2-(6-Aminopyrid-3-yl)-4-(1,1-dimethylethyl)morpholine Citrate

A solution of 1.66 g of 2-(tetrazolo[1,5-a]pyrid-6-yl)-4-(1,1-dimethylethyl)morpholine, 2.86 g of $SnCl_2.2H_2O$ and 0.25 ml of 12M hydrochloric acid in 150 ml of methanol was heated t reflux for 20 hours. The reaction mixture was concentrated under reduced pressure and then poured into ice water containing 5N sodium hydroxide and methylene chloride. The layers were separated and the aqueous phase further extracted with methylene chloride. The combined organic extracts were washed with water and saturated sodium chloride. The organic solution was dried with anhydrous magnesium sulfate and then concentrated to give an oil, 1.43 g.

This crude product was chromatographed on silica gel (95:5:1 methylene chloride:ethanol:ammonium hydroxide) to give 1.39 g of pure product. $^{13}C$ NMR spectrum: 25.4 45.3 52.9 53.6 67.5 76.5 108.0 126.0 136.0 146.1 158.1 ppm.

A solution of this material (1.33 g) in 4 ml of ethanol was added dropwise to a cold solution of citric acid (1.08 g) in 20 ml of ethanol. The salt was permitted to stir for 30 minutes and then diluted with ether. The salt was collected buy filtration and dried to give 2.40 g of product, m.p. 164°-66° C.

EXAMPLE 4

2-(6-Aminopyrid-3yl)-4-(1,1-dimethylethyl)-5-oxo-morpholine

A solution of 2-(tetrazolo[1,5-a]pyrid-6-yl)-4-(1,1-dimethylethyl)-5-oxo-morpholine (550 mg), $SnCl_2.2H_2O$ (968 mg) and 0.2 ml of 12N hydrochloric acid in 60 ml of methanol was heated at reflux for 14.5 hours under nitrogen. The reaction mixture was concentrated under reduced pressure and then poured into ice water containing 5N sodium hydroxide. The basic aqueous mixture was repeatedly extracted with methylene chloride. The combined organic fractions were washed with water and saturated sodium chloride solution and then dried over anhydrous magnesium sulfate. Concentration gave 603 mg of crude product which was chromatographed on silica gel (95:5:1 methylene chloride:ethanol:ammonium hydroxide) to give 442 mg of product. Mass spectrum (FAB) 250 (M+1). $^{13}C$ NMR (CDCl$_3$) 27.9 49.5 57.7 69.2 74.3 108.5 123.6 135.8 146.3 158.7 167.4 ppm.

EXAMPLE 5

2-(2-Aminopyrimid-5-yl)-4-(1,1-dimethylethyl)-5-oxo-morpholine

To a cold solution of 2-isobutyramido-60-{[(1,1-dimethylethyl)amino]methyl-5-pyrimidinemethanol (2.38 mmol) and triethylamine in 10 ml of dry methylene chloride, a solution of chloroacetyl chloride (2.62 mmol) in 1 ml of methylene chloride is added dropwise under nitrogen. The reaction mixture is stirred overnight at ambient temperature. The reaction mixture is concentrated under reduced pressure. The residue is partitioned between ethyl acetate and water. The organic phase is dried with magnesium sulfate and concentrated. The residue is dissolved in ethanol and treated with an ethanolic solution of sodium ethoxide/sodium hydroxide. The mixture is heated at reflux for 5 hours and then concentrated under reduced pressure. The residue is partitioned between ethyl acetate and water. The organic layer is washed with water and brine and then dried with magnesium sulfate. Concentration and chromatography on silica gel affords the desired product.

EXAMPLE 6

2-(2-Aminopyrimid-5-yl)-4-(1,1-dimethylethyl)morpholine

To a solution of 2-(2-aminopyrimid-5-yl)-4-(1,1-dimethylethyl)-5-oxo-morpholine (2.0 g) in 100 ml of dry tetrahydrofuran, 10 ml of a 2.0M solution of $BH_3.Me_2S$ in tetrahydrofuran is added dropwise under nitrogen. The reaction mixture is then heated at reflux for 5 hours followed by treatment with methanol (25 ml) at reflux for 3 hours. The solution is concentrated and the residue chromatographed on silica gel to give the titled compound.

EXAMPLE 7

2-(4-Chloro-tetrazolo1,5-a]pyrid-6-yl)-4-(1,1-dimethylethyl)-5-oxo-morpholine

To a cold (0° C.) solution of α-[[(1,1-dimethylethyl)-amino)methyl]tetrazolo[1,5-a]pyridine-4-chloro-6-methanol (2.9 g) and triethylamine in 50 ml of dry (3A sieves) methylene chloride, a solution of chloroacetyl chloride (1.3 g) in 3 ml of methylene chloride is added dropwise under nitrogen. The reaction mixture is stirred at 0° C. for 1 hour and then overnight at ambient temperature. The reaction mixture is concentrated under reduced pressure and the residue dissolved in ethyl acetate and washed with water. The organic phase is dried with anhydrous magnesium sulfate and concentrated to give the crude N-chloroacetyl derivative. To an ethanolic solution (40 ml) of this crude product, a solution of sodium ethoxide in ethanol (0.27 g of sodium in 40 ml of absolute ethanol) is slowly added. The resulting solution is heated at reflux under nitrogen for 7 hours. The reaction mixture is concentrated under reduced pressure and the residue partitioned between ethyl acetate and water. The aqueous phase is repeatedly extracted with ethyl acetate and the combined organic layers are washed with saturated sodium chloride solution, dried over anhydrous magnesium sulfate and concentrated to give crude cyclized product. The material is purified by chromatography on silica gel to give the titled compound.

EXAMPLE 8

2-(4-Chloro-tetrazolo[1,5-a]pyrid-6-yl)-4-(1,1dimethylethyl)morpholine

To a solution of 2-(4-chloro-tetrazolo[1,5-a]pyrid-6-yl)-4-(1,1-dimethylethyl)-5-oxo-morpholine (1.0 g) in 50 ml of dry tetrahydrofuran (THF), a 2.0M solution of $BH_3.Me_2S$ in tetrahydrofuran (5 ml) is added dropwise under nitrogen. The reaction mixture is heated at reflux for 5 hours and then treated with 25 ml of methanol. The resulting mixture is heated at reflux for 3 hours, concentrated and chromatographed to afford the title compound.

EXAMPLE 9

2-(6-Amino-5-chloropyrid-3-yl)-4-(1,1-dimethylethyl)-morpholine

A solution of 0.83 g of 2-(4-chloro-tetrazolo[1,5-a]pyrid-6-yl)-4-(1,1-dimethylethyl)morpholine 1.42 g of $SnCl_2.2H_2O$ and 0.15 ml of 12M hydrochloric acid in 75 ml of methanol is heated at reflux for 20 hours. The reaction mixture is concentrated under reduced pressure and then poured into ice water containing 5N sodium hydroxide and methylene chloride. The layers are separated and the aqueous phase further extracted with methylene chloride. The combined organic extracts are washed with water and saturated sodium chloride. The organic solution is dried with anhydrous magnesium sulfate and concentrated. The residue is chromatographed on silica gel to give the title compound.

What is claimed is:
1. A compound having the formula

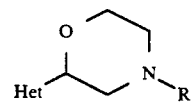

wherein
Het is

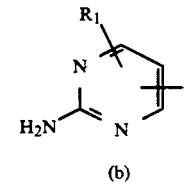

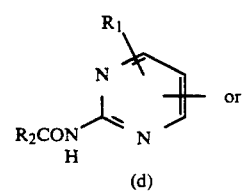

R is loweralkyl, cycloloweralkyl, substituted aralkyl, heterocyclicloweralkyl or substituted heterocyclicloweralkyl;
$R_1$ is hydrogen, halogen or cyano;
$R_2$ is lower alkyl, phenyl, substituted phenyl, phenyl-lower alkyl; and pharmaceutically acceptable salts thereof.

2. The compounds of claim 1 wherein Het is structure (b).

3. The compounds of claim 2 wherein R is loweralkyl of from 3 to 6 carbon atoms; or aralkyl where the alkyl portion is from 3 to 6 carbon atoms and the aryl portion is phenyl, methoxy phenyl or hydroxy phenyl; or heterocyclicloweralkyl where the heterocyclic portion is indolyl, methoxyindolyl or hydroxy indolyl, and the loweralkyl portion is from 3 to 6 carbon atoms; and $R_1$ is hydrogen or halogen.

4. The compounds of claim 3 wherein the loweralkyl, and the loweralkyl portions of the aralkyl and heterocyclic lowerarlkyl is a lowerally with an α-branched methyl or ethyl or an α-branched gem dimethyl or diethyl substitution pattern.

5. The compounds of claim 4 wherein R is tert-butyl, 1,1-dimethylpropyl optionally substituted with phenyl or indolyl and where said phenyl and indolyl may be optionally substituted with hydroxy or methoxy; and $R_1$ is hydrogen or chloro.

6. The compounds of claim 1 which are the hydrochloride, maleate or citrate salts thereof.

7. The compound of claim 1 which is 2-(2-aminopyrimid-5-yl)-4-(1,1-dimethylethyl) morpholine.

8. A method for the promotion of growth and increasing the feed efficiency of animals which comprises administering to such animals an effective amount of a compound of claim 1.

9. A composition useful for promoting the growth and increasing the feed efficiency of animals which comprises an inert carrier and a compound of claim 1.

10. A method for promoting bronchodilation which comprises administering to patients in need of bronchodilation an effective amount of a compound of claim 1.

11. A composition useful for promoting bronchodilation which comprises an inert carrier and a compound of claim 1.

12. A method for treating the symptoms of depression which comprises administering to a patient with depression an effective amount of a compound of claim 1.

13. A composition useful for treating the symptoms of depression which comprises an inert carrier and a compound of claim 1.

14. A method for treating obesity which comprises administering to an obese patient an effective amount of a compound of claim 1.

15. A composition useful for treating obesity which comprises an inert carrier and a compound of claim 1.

* * * * *